US006521223B1

(12) United States Patent
Calias et al.

(10) Patent No.: US 6,521,223 B1
(45) Date of Patent: Feb. 18, 2003

(54) SINGLE PHASE GELS FOR THE PREVENTION OF ADHESIONS

(75) Inventors: Pericles Calias, Melrose; Robert J. Miller, Halifax, both of MA (US)

(73) Assignee: Genzyme Corporation, Cambridge, MA (US)

( * ) Notice: Subject to any disclaimer, the term of this patent is extended or adjusted under 35 U.S.C. 154(b) by 0 days.

(21) Appl. No.: 09/503,544

(22) Filed: Feb. 14, 2000

(51) Int. Cl.[7] .......................... A61K 31/74; A61K 9/00; A61K 47/00; A61F 13/00; A61F 2/00
(52) U.S. Cl. ................... 424/78.08; 424/422; 424/423; 424/400; 514/781
(58) Field of Search .............................. 424/78.08, 400, 424/422, 423; 524/29; 514/781

(56) References Cited

U.S. PATENT DOCUMENTS

| | | |
|---|---|---|
| 3,106,439 A | 10/1963 | Valentine et al. |
| 3,316,308 A | 4/1967 | Welch |
| 3,357,784 A | 12/1967 | Kasper |
| 4,178,361 A | 12/1979 | Cohen et al. |
| 4,582,865 A * | 4/1986 | Balazs et al. ................. 524/29 |
| 4,605,691 A | 8/1986 | Balazs et al. |
| 4,636,524 A | 1/1987 | Balazs et al. |
| 4,713,448 A | 12/1987 | Balazs et al. |
| 4,716,154 A | 12/1987 | Mälson et al. |
| 4,937,270 A | 6/1990 | Hamilton et al. |
| 5,017,229 A * | 5/1991 | Burns et al. ................. 424/488 |
| 5,099,013 A | 3/1992 | Balazs et al. |
| 5,128,326 A | 7/1992 | Balazs et al. |
| 5,143,724 A | 9/1992 | Leshchiner et al. |
| 5,219,360 A | 6/1993 | Georgiade |
| 5,246,698 A | 9/1993 | Leshchiner et al. |
| 5,399,351 A | 3/1995 | Leshchiner et al. |
| 5,527,893 A | 6/1996 | Burns et al. |
| 5,676,694 A | 10/1997 | Della Valle et al. |
| 5,760,200 A | 6/1998 | Miller et al. |
| 5,783,691 A | 7/1998 | Mälson et al. |
| 6,030,958 A | 2/2000 | Burns et al. |
| 6,066,325 A * | 5/2000 | Wallace et al. ............. 424/400 |
| 6,086,907 A | 7/2000 | Goldberg et al. |
| 6,174,999 B1 * | 1/2001 | Miller et al. .................. 514/60 |
| 6,235,726 B1 | 5/2001 | Burns et al. |
| 6,294,202 B1 | 9/2001 | Burns et al. |

FOREIGN PATENT DOCUMENTS

| | | |
|---|---|---|
| EP | 0 224 987 | 6/1987 |
| EP | 0 732 110 | 9/1996 |
| EP | 0 939 086 * | 1/1999 |
| GB | 2 151 244 | 7/1985 |
| WO | WO 86 00079 | 1/1986 |
| WO | WO 86 00912 | 2/1986 |
| WO | WO 86 04355 | 7/1986 |

OTHER PUBLICATIONS

US 5,808,050, 9/1998, Mares-Guia (withdrawn)*
Danishefsky et al., Conversion of Carboxyl Groups of Mucopolysaccharides Into Amides of Amino Acid Esters, *Carbohydrate Research*, vol. 16, pp. 199–205 (1971).
Sparer et al., Controlled Release from Glycosaminoglycan Drug Complexes, *Controlled Release Delivery Systems*, Chapter 6, pp. 107–119 (1983).
Larsen, N. E., et al., "Hylan Gel Biomaterial: Dermal and Immunologic Compatibility", *J. Biomedical Materials Research*, 27: 1129–1134 (1993).
Burns, J., et al., Preclinical Evaluation of Seprafilm ™ Bioresorbable Membrane, *Eur. J. Surg.*, Suppl. 577: 40–48 (1997).

* cited by examiner

*Primary Examiner*—Thurman K. Page
*Assistant Examiner*—Blessing Fubara
(74) *Attorney, Agent, or Firm*—Isabelle A. S. Blundell

(57) ABSTRACT

Single phase gels for preventing the formation of surgical adhesions are disclosed. The gels are prepared by reacting an aqueous solution of a polyanionic polysaccharide, such as hyaluronic acid or carboxymethyl cellulose, with divinyl sulfone, to form a gel, the solution is neutralized, and a solid is precipitated from the solution. The solid can be redissolved in water to form a gel having properties which can be modified to suit a particular application.

15 Claims, No Drawings

SINGLE PHASE GELS FOR THE PREVENTION OF ADHESIONS

Throughout this application, various publications are referenced. All publications referenced herein, including published patent applications and issued or granted patents, are hereby incorporated by reference in their entireties into this application.

BACKGROUND OF THE INVENTION

This invention relates to single phase gel products formed by the reaction of a polyanionic polysaccharide and divinyl sulfone ("DVS"), and preferably formed by the reaction of hyaluronic acid ("HA") and divinyl sulfone. The single phase gel products of this invention are particularly useful for preventing the formation of adhesions between affected tissue surfaces of a subject who has undergone a surgical procedure.

Adhesion formation is a well known complication of many types of surgical procedures, and particularly abdominal and bowel surgeries. Adhesion formation typically occurs as a result of the formation of a fibrin clot which transforms into scar tissue connecting different tissues which are normally separated. Surgical intervention is frequently required in order to eliminate the adhesions, although the adhesions can, and often do, reappear following the surgery. The primary objective of adhesion prevention formulations is to interrupt the adhesion formation mechanism, which is believed to result from the diffusion of fibrinogen into the space between the tissues subject to surgical trauma, thereby causing the formation of fibrin clots in the space.

In addition to acting as an adhesion barrier, a successful anti-adhesion formulation should be "biocompatible", meaning that it has no medically unacceptable toxic or injurious effects on the biological function of the subject, and "bioabsorbable", meaning that it can be absorbed by the tissue without remaining in the subject as an implant device. Thus, the formulation should remain in the body for a sufficient period of time to be effective in separating the tissue and preventing adhesions, while being absorbed by the tissue once the danger of adhesion formation has ended, thereby minimizing any long term effects which may result from the use of an implant device.

Hyaluronic acid ("HA") is a naturally occurring mucopolysaccharide found, for example, in synovial fluid, in vitreous humor, in blood vessel walls, the umbilical cord, and in other connective tissues. The polysaccharide consists of alternating N-acetyl-D-glucosamine and D-glucuronic acid residues joined by alternating β1–3 glucoronidic and β1–4 glucosaminidic bonds, so that the repeating unit is —(1→4)-β-D-G1cA-(1→3)-βD-G1cNAc-. In water, hyaluronic acid dissolves to form a highly viscous fluid. The molecular weight of hyaluronic acid isolated from natural sources generally falls within the range of from about $5 \times 10^4$ up to about $1 \times 10^7$ daltons.

Hyaluronic acid, in chemically modified form, is known to be useful as a surgical aid to prevent adhesions and accretions of body tissues during the post-operation period. The chemically modified hyaluronic acid gel or film is injected or inserted into the locus between the tissues that are to be kept separate to inhibit their mutual adhesion. Chemically modified hyaluronic acid can also be useful for controlled release drug delivery. See U.S. Pat. No. 4,937,270 and U.S. Pat. No. 5,017,229, which disclose chemically modified versions of HA, or HA in combination with other polyanionic polysaccharides, such as carboxymethylcellulose, which are prepared by reacting the HA with a carbodiimide. The chemically modified version of HA and carboxymethylcellulose is commercially available in film form as Seprafilm® membranes from the Genzyme Corporation.

I. Danishefsky et al., *Carbohydrate Res.*, Vol. 16, pages 199–205, 1971, describe the modification of a mucopolysaccharide by converting the carboxyl groups of the mucopolysaccharide into substituted amides by reacting the mucopolysaccharide with an amino acid ester in the presence of 1-ethyl-3-(3-dimethylaminopropyl) carbodiimide hydrochloride ("EDC") in aqueous solution. Danishefsky et al. react glycine methyl ester with a variety of polysaccharides, including HA. The resulting products are water soluble; that is, they rapidly disperse in water or in an aqueous environment such as is encountered between body tissues.

Proposals for rendering HA compositions less water soluble include cross-linking the HA. R. V. Sparer et al., 1983, Chapter 6, pages 107–119, in T. J. Roseman et al., *Controlled Release Delivery Systems*, Marcel Dekker, Inc., New York, describe modifying HA by attaching cysteine residues to the HA by amide bonds, and then cross-linking the cysteine-modified HA by forming disulfide bonds between the attached cysteine residues.

U.S. Pat. No. 5,676,964 describes the preparation of cross-linked polysaccharides, including HA, wherein the cross-linking reaction occurs as a result of covalent bonds formed between carboxyl groups and hydroxyl groups of adjacent polysaccharide molecules.

U.S. Pat. No. 4,582,865; U.S. Pat. No. 4,636,524 and U.S. Pat. No. 5,128,326 describe HA compositions in which the HA is cross-linked by reaction with divinyl sulfone, and further describe the use of these compositions for drug delivery applications. U.S. Pat. No. 4,605,691 describes a method for preparing cross-linked HA compositions using divinyl sulfone as a cross-linking agent in an alkali solution.

U.S. Pat. No. 5,143,724; U.S. Pat. No. 5,247,698 and U.S. Pat. No. 5,399,351 disclose biocompatible, viscoelastic polymeric gel slurries prepared by reacting hyaluronic acid and a cross-linking agent such as divinyl sulfone, which are used in anti-adhesion formulations. The gel slurry is a two phase composition comprising discrete particles distributed in a polymer solution. In one embodiment, the slurry is formed from cross-linked hyaluronic acid particles contained in a solution of hyaluronic acid. The two phase slurries are believed to be effective in preventing adhesion formation due to their ability to separate affected tissue surfaces coupled with the ability to restrict diffusion at the site of potential adhesion formation.

U.S. Pat. No. 5,783,691 relates to hyaluronic acid compositions which are prepared by crosslinking hyaluronic acid with a phosphorus-containing reagent, such as sodium phosphate, in an alkaline medium to form a gel product. The crosslinking reagents described in this patent are not completely soluble, resulting in a two phase system, with one phase containing the crosslinked product. The gels can contain drugs and can be used as drug release vehicles upon administration to a subject.

Two phase gel slurries do suffer from certain drawbacks, however. For instance, the material must be processed correctly in order to improve the handling properties of the material, and to permit its therapeutic application through the narrow openings of needles and other applicators, particularly for minimally invasive surgical indications. Such processing requires the use of processing equipment and the application of shear forces to the material, which in turn can result in a decrease in viscosity (thinning). Two phase materials contain dispersed, heterogeneous particles which tend to plug the narrow openings of such delivery systems. A single phase, homogeneous composition is more useful in minimally invasive surgical applications where devices are introduced into the body through narrow access ports.

It would therefore be highly desirable to formulate a single phase gel solution which is capable of preventing the formation of adhesions, and which can be easily handled and stored for future use, and which possesses the advantageous characteristics of two phase gels.

SUMMARY OF THE INVENTION

The present invention features a cross-linked polyanionic composition which is useful for the prevention of adhesions which can arise as the result of a surgical procedure performed on a subject. The cross-linked composition is prepared by the reaction of the polyanionic polysaccharide with divinyl sulfone. The reaction occurs in an aqueous solution and results in the formation of a gel. The gel solution is neutralized, preferably by acidifying the solution, and a solid is precipitated from the solution. The solid can be pulverized to form a powder, and subsequently rehydrated with water to form a single phase, purified gel having properties suitable for use in anti-adhesion formulations.

In one embodiment, the invention features a method for preparing a single phase gel for use in preventing the formation of surgical adhesions. The gels of this invention are prepared by reacting a polyanionic polysaccharide with divinyl sulfone to form a cross-linked gel. Preferably, the polyanionic polysaccharide is hyaluronic acid or carboxymethyl cellulose, and the molar ratio of divinyl sulfone to polyanionic polysaccharide is from about 0.1:1 to about 1:1, and more preferably from about 0.2:1 to about 0.6:1. The gel is neutralized by the addition of an acidic compound, such as an inorganic acid, typically hydrochloric acid or sulfuric acid, to an aqueous solution of the gel and the cross-linking agent. The gel can be precipitated as a solid, preferably as a powder or fine particles, and stored until it is desired to reconstitute the gel by rehydration of the powder.

Terminal sterilization of the gel can be accomplished by autoclaving the gel, and this procedure does not have any substantial adverse impact on the gel structure. Terminal sterilization is a cost effective method for manufacturing a medical device since it can assure a lower bioburden than aseptic processing, and thereby reduces the risk of infection. Typically, terminal sterilization involves steam autoclaving of aqueous preparations, and either ethylene oxide treatment or high energy bombardment (irradiation or E beam treatment) of the material in solid or dry form.

In one aspect of this embodiment, the properties of the gel are modified by subjecting the gel to heat treatment at a temperature in the range of from about 100° C. to about 150° C. Heat treatment has the effect of modifying the properties of the gel, such as its viscosity. The effect of the heat treatment on specific polymers is generally not predictable in advance, and is based on such factors as the relative degree of cross-linking. Heat treatment of a gel material can be employed to alter the final viscosity of the gel by either causing more polymer to dissolve in solution, which tends to increase the viscosity, or by reducing the molecular weight of the polymer, which tends to reduce the viscosity. Thus, adjustments to the gel viscosity can be easily carried out using this approach.

In another embodiment, the invention features a method for preventing the formation of adhesions by applying the cross-linked gel prepared according to the method of this invention to the surface of the tissue which is exposed during a surgical procedure and which is in proximity to the site of the procedure.

The composition can be advantageously applied to the tissue surfaces using non-invasive means, such as by means of endoscopic instruments. Minimally invasive surgical techniques are less traumatic to the patient, more cosmetically appealing, allow faster recovery times, and have lower risks of infection. The alternative to endoscopic surgery is an open surgical procedure, such as laparotomy, involving long incision lines and the risk of infection.

Sufficient material should be used to separate the tissue surfaces that may potentially develop adhesions. The gels of this invention remain in place for at least about 7 days, but no more than about 30 days, which is a sufficient period of time to prevent the formation of the adhesions. The gels of this invention are bioabsorbable, and are not toxic or injurious to the patient. These gels are also water-insoluble, due to the cross-linking, which enables the gels to remain in the body without being immediately absorbed.

In a further embodiment, a drug substance may be incorporated in the gel for delivery to the tissue at the site of the surgery. Such drug substances include, for instance, NSAIDS, lidocaine, and derivatives thereof, steroids, growth factors, cytokines, antibiotics, etc., and the like.

Unless defined otherwise, all technical and scientific terms used herein have the same meaning as commonly understood by one of ordinary skill in the art to which this invention pertains. Although any methods and materials similar or equivalent to those described herein can be used in the practice or testing of the present invention, the preferred methods and materials are now described. Unless mentioned otherwise, the techniques employed or contemplated herein are standard methodologies well known to one of ordinary skill in the art. The materials, methods and examples are illustrative only, and are not intended to be limiting. Other features and advantages of the invention will be apparent from the following detailed description, and from the appended claims.

DETAILED DESCRIPTION OF THE INVENTION

The present invention provides a method for preparing a water insoluble biocompatible composition comprising reacting a polyanionic polysaccharide with divinyl sulfone in an aqueous solution to form a gel, neutralizing the pH of the solution, and precipitating a solid from the solution. The polyanionic polysaccharide used may be selected from the group consisting of hyaluronic acid, sodium hyaluronate, potassium hyaluronate, magnesium hyaluronate, calcium hyaluronate, carboxymethylcellulose, carboxymethyl amylose and a mixture of hyaluronic acid and carboxymethylcellulose. In one embodiment of the invention, the solid precipitated from the solution is then rehydrated to form a gel. The invention further provides that the rehydrated gel may then be subjected to heat treatment. In one embodiment, the rehydrated gel is heated to a temperature in the range from about 100° C. to about 150° C.

The present invention also provides a method for preparing a water insoluble biocompatible composition comprising reacting a polyanionic polysaccharide with divinyl sulfone in an aqueous solution to form a gel, neutralizing the pH of the solution, and precipitating a solid from the solution wherein the polyanionic polysaccharide is hyaluronic acid. In one embodiment, the molar ratio of divinyl sulfone:hyaluronic acid is from about 0.1:1 to about 1:1. In another embodiment, the molar ratio of divinyl sulfone:hyaluronic acid is from about 0.2:1 to about 0.6:1.

The present invention also provides for a single phase gel product formed by any of the methods of the invention herein described. The single phase gel product of the invention may be sterilized. The single phase gel product of the invention may further comprise a drug.

The present invention also provides for a method for the prevention of adhesions in a subject comprising applying the gel product of the invention to a region between two tissue surfaces to be separated during the healing process following surgery. The subject may be a human patient.

Additionally, the surgery being performed on the subject may be one selected from the group consisting of abdominal surgery, pelvic surgery, gynecological surgery, orthopedic surgery, and cardiac surgery.

As used herein, and unless otherwise indicated, the term "polyanionic polysaccharide" denotes a polysaccharide containing more than one negatively charged group, e.g., carboxyl groups at pH values above about pH 4.0. This includes hyaluronic acid ("HA"), any of its hyaluronate salts, including, for example, sodium hyaluronate (the sodium salt), potassium hyaluronate, magnesium hyaluronate, and calcium hyaluronate, carboxymethylcellulose ("CMC"), and mixtures of hyaluronic acid and carboxymethylcellulose, and carboxymethyl amylose.

A "biocompatible" substance, as the term may be used herein, is one that has no medically unacceptable toxic or injurious effects on biological function.

A "bioabsorbable" substance is one which is maintained in the body in a relatively intact form for at least about 7 days, and is then completely absorbed by the body after about 30 days thereafter. A bioabsorbable substance is thus not considered to be an "implant", which remains in the body for more than about 30 days without decomposition. A bioabsorbable substance does not have to meet the more stringent is FDA requirement imposed on implants.

A "cross-linked polyanionic polysaccharide" is a polyanionic polysaccharide which has been reacted with a divinyl sulfone cross-linking agent to form a 3-dimensional network by covalent bonding between the divinyl sulfone and reactive sites on adjacent polymers. The degree of cross-linking can be measured by the amount of cross-linking agent consumed in the cross-linking reaction.

The expression "preventing adhesion formation" is intended to encompass not only the complete elimination of adhesions, but the substantial reduction in the amount or number of adhesions formed as compared to the amount or number of adhesions formed using a control substance such as saline, or the absence of any treatment to reduce the level of adhesions.

A "gel" is a colloidal suspension of a dispersed solid phase in a continuous phase. In the context of this invention, the dispersed solid phase comprises particles of a polyanionic polysaccharide, and the continuous phase is water. A "water soluble" gel, as that term is used herein, is a gel which as an aqueous 1% weight/weight ("w/w") solution of the cross-linked polyanionic polysaccharide gel, when placed in a 50 mL beaker of distilled water maintained at about 20° C., and allowed to stand without stirring, dissolves completely into a single phase within 20 minutes. A "water insoluble" gel is a gel which, when prepared under the conditions as described for a water soluble gel, is structurally intact after 20 minutes. The gels of the present invention are water insoluble, enabling them to function as effective adhesion reduction devices.

A solution is "neutralized" when the pH value of the solution is adjusted so that the final pH of the solution is approximately 7.0, or alternatively, in the range of from about 6.0 to about 8.0. The relatively alkaline solutions of the present invention are adjusted by lowering the pH by the addition of an acidic compound to the reaction mixture of the polyanionic polysaccharide and divinyl sulfone.

The anti-adhesion formulations of this invention can be prepared from a polyanionic polysaccharide which is cross-linked by reaction with divinyl sulfone. The reactants can be dissolved in water at a basic pH, preferably at a pH of about 12, and the reaction is allowed to proceed until a gel is formed. The mode of addition of the reagents is not critical to the reaction.

The amount of divinyl sulfone consumed in the cross-linking reaction generally varies from about 0.1 moles of DVS up to 1.0 mole of DVS per mole of polyanionic polysaccharide. Lower amounts of DVS produce lightly cross-linked gels which tend to be more soluble, while higher amounts of DVS produce more tightly cross-linked gels which tend to be more insoluble.

The preferred polyanionic polysaccharides are hyaluronic acid and carboxymethyl cellulose. Hyaluronic acid, or its salts such as sodium hyaluronate, is readily soluble in water. HA from any of a variety of sources can be used. For instance, HA can be extracted from animal tissues, such as rooster combs, or harvested as a product of bacterial fermentation. HA can be produced in commercial quantities using bioprocess technology, as described for example in PCT Publication No. WO 86/04355.

The product formed from the reaction of HA and DVS is then mixed with water, and the pH of the mixture is adjusted to an approximately neutral level, e.g. about 7.0, or from about 6.0 to about 8.0, by the addition of an acidic compound to the solution. Suitable acids include sulfuric acid and hydrochloric acid.

The gel is then precipitated with ethanol as a solid. Preferably, the gel is pulverized to form a powder, which can be stored until it is needed for medical use. The powder can be easily reconstituted by rehydration, and optionally subjected to heat treatment to adjust the rheological properties to achieve the desired physical characteristics.

From the above description, one skilled in the art can readily ascertain the essential characteristics of the present invention, and without departing from the spirit and scope of thereof, can make various changes and modifications of the invention to adapt it to various usages and conditions.

As one skilled in the art will appreciate, the gels of this invention can be made using methods which may differ in certain particulars from those methods exemplified herein. For example, when precipitating the solid from solution, any water miscible solvent having a lower polarity than water may be used. Suitable solvents include, for example, ethanol, isopropyl alcohol and acetone.

The following examples of the invention are provided by way of illustration only, and are not intended to limit the invention as set forth in the appended claims.

EXAMPLE 1

200 mL of a 0.2 N sodium hydroxide solution was added to 8.0 grams of hyaluronic acid (19.95 mmol), and the mixture was stirred at room temperature until it fully dissolved (about 3 hours). 266 mL of divinyl sulfone (4.0 mmol) was added to the hyaluronic acid solution and vigorously stirred for about one minute. The reaction mixture was allowed to stand at room temperature for one hour. The resulting gel was placed in D.I. water for 24 hours, and then chopped into quarters, and allowed to stand in PBS for an additional 24 hours. 5 mL of PBS was added to the swollen gel, and the mixture was mixed under high sheer conditions. The pH of the solution was then adjusted to 7.2 with 6 N hydrochloric acid, followed by precipitation with absolute ethanol (3.0 L). The white precipitate was collected and dried under vacuum. The powder is easily rehydrated upon the addition of PBS and high shear mixing.

Following this procedure, hyaluronic acid gels can be synthesized with varying amounts of divinyl sulfone and reconstituted at different concentrations (expressed as % solid per volume, where 1% equals 1 gram/100 mL) to obtain a desired Theological property. The results are shown in Tables I, II and III below for gels having DVS:HA molar ratios of 0.2:1, 0.3:1 and 0.6:1, respectively, before and after heat treatment at 121° C. for 20 minutes, where the numbers in parentheses indicate the values before heat treatment.

TABLE I

DVS:HA Mole Ratio of 0.2:1

| Conc. (%) | Phase Angle (°) | Complex Modulus (Pa) | Yield Stress (Pa) | Viscosity (cP) |
|---|---|---|---|---|
| 1.0 | (42.9) 49.00 | (9.3) 6.6 | (3.8) 1.9 | (3,739) 2,189 |
| 1.5 | (40.7) 45.00 | (36.9) 26 | (11.6) 7.8 | (20,630) 13,400 |
| 2.0 | (36.3) 40.00 | (54.4) 42 | (13.6) 11.7 | (31,900) 24,000 |
| 2.5 | (28.8) 37.00 | (269) 99 | (68) 19.7 | (183,580) 59,100 |

TABLE II

DVS:HA Mole Ratio of 0.3:1

| Conc. (%) | Phase Angle (°) | Complex Modulus (Pa) | Yield Stress (Pa) | Viscosity (cP) |
|---|---|---|---|---|
| 1.0 | (42.8) 44.6 | (15.44) 9.66 | (3.9) 1.98 | (7,267) 3,103 |
| 1.5 | (36.9) 45.2 | (32.65) 23.01 | (9.72) 9.66 | (16,776) 12,937 |
| 2.0 | (29.0) 38.9 | (81.84) 61.68 | (21.6) 9.66 | (53,728) 40,547 |
| 2.5 | (31.8) 39.9 | (72.84) 56.097 | (19.6) 17.6 | (49,495) 35,940 |

TABLE III

DVS:HA Mole Ratio of 0.6:1

| Conc. (%) | Phase Angle (°) | Complex Modulus (Pa) | Yield Stress (Pa) | Viscosity (cP) |
|---|---|---|---|---|
| 1.0 | (27.4) 34.6 | (19.57) 13.59 | (1.99) 3.92 | (9,093) 8,178 |
| 1.5 | (25.2) 27.2 | (38.56) 48.02 | (11.8) 17.6 | (26,213) 43,885 |
| 2.0 | (22.4) 26.9 | (55.43) 60.22 | (15.6) 23.5 | (45,670) 55,438 |
| 2.5 | (22.4) 26.9 | (130.43) 141.28 | (33.3) 46.9 | (147,150) 160,852 |

The Tables above show that the gels become more resistant to degradation by heat as the amount of cross-linking is increased. The gels made using a 0.6:1 DVS:HA molar ratio are quite stable to heat treatment, which directly correlates to the stability of the gels under autoclave conditions.

EXAMPLE 2

200 mL of a 0.2 N sodium hydroxide solution was added to 8.0 grams of hyaluronic acid (19.95 mmol), and the mixture was stirred at room temperature until it fully dissolved (about 3 hours). 396 mL of divinyl sulfone (5.99 mmol) was added to the hyaluronic acid solution and vigorously stirred for about one minute. The reaction mixture was allowed to stand at room temperature for one hour. The resulting gel was placed in D.I. water for 24 hours, and then chopped into quarters, and allowed to stand in PBS for an additional 24 hours. 5 mL of PBS was added to the swollen gel, and the mixture was mixed under high sheer conditions. The pH of the solution was then adjusted to 7.2 with 6 N hydrochloric acid, followed by precipitation with absolute ethanol (3.0 L). The white precipitate was collected and dried under vacuum. The powder is easily rehydrated upon the addition of PBS and high shear mixing.

EXAMPLE 3

200 mL of a 0.2 N sodium hydroxide solution was added to 8.0 grams of hyaluronic acid (19.95 mmol), and the mixture was stirred at room temperature until it fully dissolved (about 3 hours). 798 mL of divinyl sulfone (12.0 mmol) was added to the hyaluronic acid solution and vigorously stirred for about one minute. The reaction mixture was allowed to stand at room temperature for one hour. The resulting gel was placed in D.I. water for 24 hours, and then chopped into quarters, and allowed to stand in PBS for an additional 24 hours. 5 mL of PBS was added to the swollen gel, and the mixture was mixed under high sheer conditions. The pH of the solution was then adjusted to 7.2 with 6 N hydrochloric acid, followed by precipitation with absolute ethanol (3.0 L). The white precipitate was collected and dried under vacuum. The powder is easily rehydrated upon the addition of PBS and high shear mixing.

EXAMPLE 4

Gels prepared from the rehydrated powder as shown in Example 1 were tested for efficacy in preventing post-operative adhesions in a rat cecal abrasion model as described in Burns et al., Eur. J. Surg. 1997, Suppl. 577, 40–48. Ten (10) rats were used in each study. Group 1 used a gel having a concentration of 1.5% of active ingredient, and Group 2 used a gel having a concentration of 2.5% of active ingredient. The results are shown in Table IV below listed as the percentage of each group with adhesions of grade greater than 2; the average incidence of adhesions, plus or minus the standard error of the mean; and the percentage of each group with no adhesions.

TABLE IV

| Group | % w/ adh. ≧ 2 | Avg. Inc. ± SEM | % w/ no adh. |
|---|---|---|---|
| Control | 80 | 1.5 ± 0.4 | 20 |
| Group 1 | 30 | 0.6 ± 0.3 | 70 |
| Group 2 | 20 | 0.2 ± 0.1 | 80 |

What is claimed is:

1. A method for preparing a water insoluble biocompatible composition comprising
    reacting a polyanionic polysaccharide with divinyl sulfone in an aqueous solution to form a gel, neutralizing the pH of the solution, and precipitating a solid from the neutral solution.

2. The method of claim 1, wherein the polyanionic polysaccharide is selected from the group consisting of hyaluronic acid, sodium hyaluronate, potassium hyaluronate, magnesium hyaluronate, calcium hyaluronate, carboxymethylcellulose, carboxymethyl amylose and a mixture of hyaluronic acid and carboxymethylcellulose.

3. The method of claim 1 or 2, wherein the solid precipitated from the solution is then rehydrated to form a gel.

4. The method of claim 3, wherein the rehydrated gel is then subjected to heat treatment.

5. The method of claim 4, wherein the rehydrated gel is heated to a temperature in the range from about 100° C. to about 150° C.

6. The method of claim 2, wherein the polyanionic polysaccharide is hyaluronic acid.

7. The method of claim 6, wherein the molar ratio of divinyl sulfone:hyaluronic acid is from about 0.1:1 to about 1:1.

8. The method of claim 7, wherein the molar ratio of divinyl sulfone:hyaluronic acid is from about 0.2:1 to about 0.6:1.

9. A single phase gel product formed by the method of claim 2, 6, 7 or 8.

10. The gel product of claim 9, which is sterilized.

11. The gel product of claim 9, which further comprises a drug.

12. The gel product of claim 10, which further comprises a drug.

13. A method for the inhibition of adhesions in a subject comprising applying the gel product of claim 9 to a region between two tissue surfaces to be separated during the healing process following surgery.

14. The method of claim 13, wherein the subject is a human patient.

15. The method of claim 14, wherein the surgery is selected from the group consisting of abdominal surgery, pelvic surgery, gynecological surgery, orthopedic surgery, and cardiac surgery.

* * * * *